United States Patent [19]

Stulen et al.

[11] 4,213,467
[45] Jul. 22, 1980

[54] MONITORING MYOELECTRIC SIGNALS

[75] Inventors: Foster B. Stulen, Somerville; Carlo De Luca, Wellesley, both of Mass.

[73] Assignee: Harvard College, President and Fellows, Cambridge, Mass.

[21] Appl. No.: 933,072

[22] Filed: Aug. 11, 1978

[51] Int. Cl.[2] .............................................. A61B 5/05
[52] U.S. Cl. .................................................. 128/733
[58] Field of Search ..................... 128/733; 307/233 R; 324/78 F; 328/167; 330/109

[56]  References Cited

U.S. PATENT DOCUMENTS

| 3,304,505 | 2/1967 | Pricer ................................. 307/233 |
| 3,638,037 | 1/1972 | McMurtrie ......................... 328/167 |
| 3,644,847 | 2/1972 | Neuman .............................. 328/167 |

OTHER PUBLICATIONS

Minkow, B. et al., "A Voltage-Controlled Filtering Technique", Intnl Jrnl Elec., vol. 38, No. 1, pp. 117–126, Jan. 1975.

DeLuca, C. J., "A Polar Technique for Displaying EMG Signals", 28 ACEMB, New Orleans, La., Sep. 20–24, 1975.

*Primary Examiner*—Robert W. Michell
*Assistant Examiner*—Francis J. Jaworski

[57] ABSTRACT

Muscle fatigue monitor featuring, in one aspect, detecting a myoelectric signal and providing an electrical output; providing a first signal corresponding to a portion of said output having frequency components above a first cutoff frequency, and a second signal corresponding to a portion of said output having frequency components below a second cutoff frequency; providing a control signal corresponding to the difference in magnitude between said first and second signals; varying said cutoff frequencies in accordance with the value of said control signal; and displaying the variation of said cutoff frequencies as a function of time.

18 Claims, 4 Drawing Figures

MONITORING MYOELECTRIC SIGNALS

FIELD OF THE INVENTION

This invention relates to continuously measuring frequency characteristics of myoelectric signals.

BACKGROUND OF THE INVENTION

It is well known in the prior art that muscles produce detectable signals. When detected with surface electrodes the myoelectric signal has a useful frequency spectrum initially between 0 Hz and 300 Hz. As the particular muscle becomes fatigued, the frequency components are compressed to lower frequencies. Accordingly, these frequencies can be monitored, e.g., to determine the effectiveness of muscle therapy, or the level of worker fatigue. E.g., in Fehmi et al. U.S. Pat. No. 3,978,847, computer analysis of a myoelectric signal is carried out to provide real time tracking of its amplitude and frequency spectrum.

Carlo J. DeLuca and W. Berenberg, "A Polar Technique for Displaying EMG Signals", (28th ACEMB, 1975) describes a monitor in which a myoelectric signal is high and low pass filtered and the resulting signals are converted to a pair of rms voltages. The filter cutoff frequencies are adjusted to provide initially equal rms voltages, and the subsequently varying voltages are then measured and displayed on a polar plot. In the actual work on which this publication was based, the initial cutoff frequency adjustment was carried out manually, requiring a recording of the myoelectric signal to be monitored.

SUMMARY OF THE INVENTION

Our invention features, in one aspect, detecting a myoelectric signal and providing an electrical output; providing a first signal corresponding to a portion of said output having frequency components above a first cutoff frequency, and a second signal corresponding to a portion of said output having frequency components below a second cutoff frequency; providing a control signal corresponding to the difference in magnitude between said first and second signals; varying said cutoff frequencies in accordance with the value of said control signal; and displaying the variation of said cutoff frequencies as a function of time.

In another aspect the invention features automatically varying said cutoff frequencies in accordance with the value of said control signal until said cutoff frequencies become initially equal to a median frequency of said output and thereafter holding said cutoff frequencies constant; and displaying the variation of said first and second signals as a function of time while said cutoff frequencies are held constant.

In preferred embodiments, the myoelectric signal is divided by modulated low pass and high pass filters having the same cutoff frequency. The divided signals from the filters are converted into two voltage levels, which are compared by a difference amplifier. An integrator receives the voltage corresponding to this difference and sends out a signal to a modulator, which feeds back its output signal to the filters. Depending upon the magnitude of the difference between the compared signals, the modulator signal raises or lowers the cutoff frequency until it equals the actual median frequency of the myoelectric signal. A muscle test can then be run and further variations in either the median frequency or the compared signals displayed.

DESCRIPTION OF PREFERRED EMBODIMENT

We turn now to the circuitry and operation of a preferred embodiment of the invention, after first briefly describing the drawings.

DRAWINGS

CIRCUITRY

Figure 1:
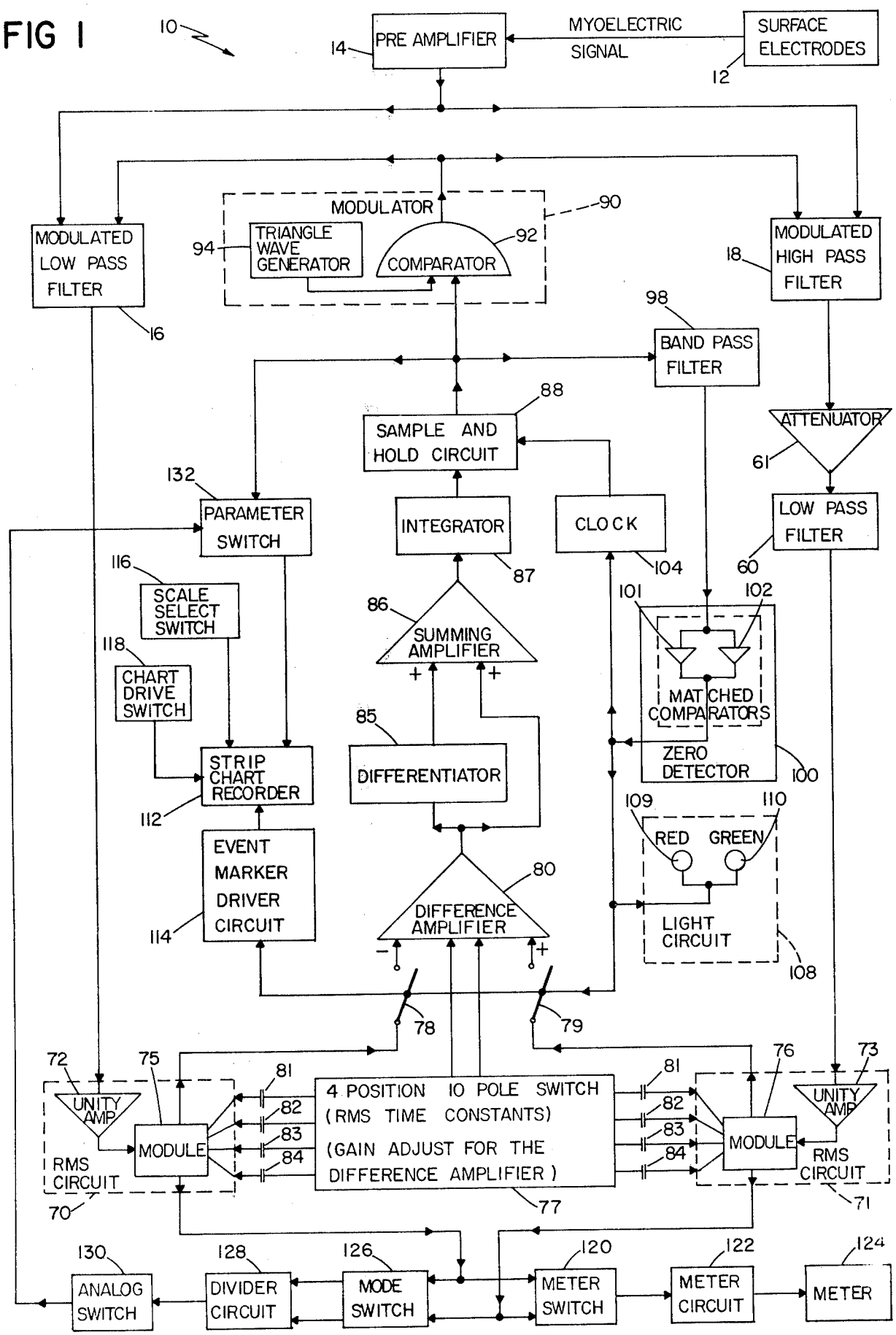
FIG. 1 is a block diagram of the circuitry embodying this invention.

Referring to FIG. 1, the muscle fatigue monitor circuit is shown generally at 10. A myoelectric signal is detected by differential surface electrodes 12 and transmitted to preamplifier 14. Preamplifier 14 first filters the myoelectric signal to remove noise and low frequency artifacts caused by body movements and then amplifies the signal.

Figure 2:
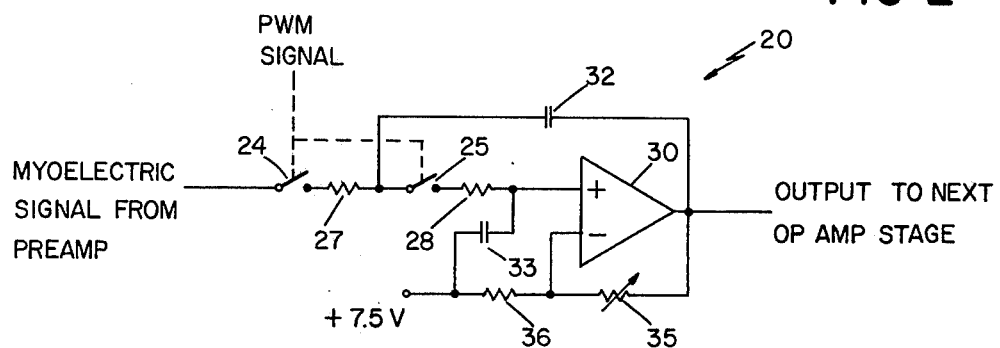
FIG. 2 is a circuit diagram of a single stage of a low pass filter.

The output from preamplifier 14 is simultaneously fed to modulated low pass and high pass filters 16, 18. Each filter has a series of five identical stages. The first stage 20 for the low pass filter is shown in FIG. 2. The signal passes through a pair of switches 24, 25 (when closed) and a pair of identical resistors 27, 28 to an input of operational amplifier 30. Identical capacitors 32, 33 form a double-pole RC filter with resistors 27, 28, which determines the cutoff frequency fc of the filter stage according to the following equation:

$$fc = n/2\pi RC$$

As the RC value is constant, the cutoff frequency is actually a function of n, the duty cycle, which is directly proportional to the length of time switches 24, 25 remain closed during a cycle. Trim resistors 35, 36 control the spectral characteristics of stage 20.

Figure 3:
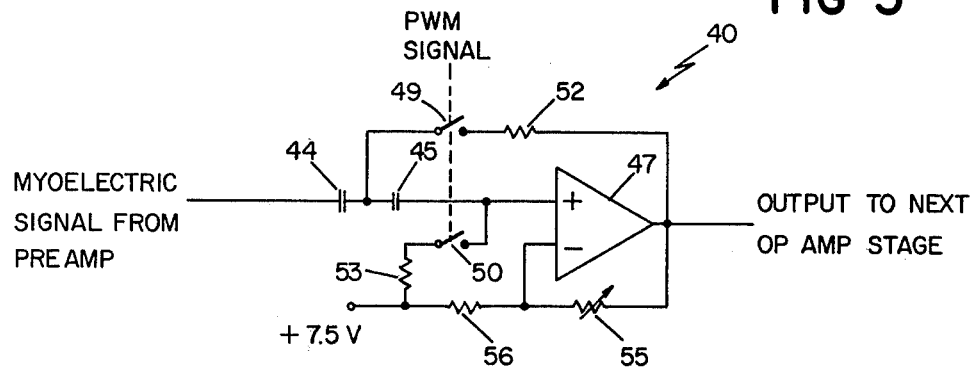
FIG. 3 is a circuit diagram of a single stage of a high pass filter.

First stage 40 for high pass filter 18 is shown in FIG. 3. The signal from preamplifier 14 passes through a pair of identical, series-connected capacitors 44, 45 to an input of operational amplifier 47. Switches 49, 50 connect a pair of resistors 52, 53 to corresponding capacitors 44, 45, and the cutoff frequency of stage 40 is governed by the same equation as with low pass filter stage 20. Trim resistors 55, 56 control the spectral characteristics of stage 40.

Low pass filter 16 has the same cutoff frequency as high pass filter 18 for all values of the duty cycle. Both filters 16, 18 have very sharp roll-offs of about 60 db per octave, and their resistor and capacitor values are correspondingly equal so that filter characteristics are independent of any change in cutoff frequency. Filters 16, 18 introduce a gain of about ten.

The output signal of high pass filter 18 is fed to fixed low pass filter 60, which removes the high frequency artifacts created by the filter's switches. As fixed low pass filter 60 introduces its own gain of about ten, an attenuator 61 is used as a pre-stage to reduce the incoming signal by the same factor. The gain of filter 60 therefore restores its output signal to a level equal to the output signal of low pass filter 16.

The signals from filters 16, 60 are fed into identical RMS circuits 70, 71, which calculate true rms voltage. RMS circuits 70, 71 have unity gain amplifiers 72, 73 as first stages, which provide the input signals for rms modules 75, 76. Amplifiers 72, 73 remove any D.C. offsets introduced by the amplifiers of filters 16, 18, and 60. Such offsets would otherwise be erroneously added to the RMS circuits' output, as each rms module 75, 76 continuously sends out an rms voltage corresponding to the magnitude of the filtered input signal it receives.

A four position switch 77 having multiple poles is connected to rms modules 75, 76 of the RMS circuits 70, 71. Two poles connect a different capacitance 81–84 to rms modules 75, 76 and thereby enables time constant of 0.1, 0.5, 2.83 or 10.0 seconds to be selected for a given test. Six other poles are used to maintain the gains and offsets of the circuits.

The outputs of RMS circuits 70, 71 are fed through switches 78, 79 (when closed) to difference amplifier 80, the output of which is proportional to the difference between its two rms voltage inputs. The gain of amplifier 80 is externally adjustable through two poles of switch 77. The gain is adjusted by the poles to keep dynamic performance constant relative to the selected time constant.

The output from amplifier 80 is sent to differentiator 85 and one input of summing amplifier 86. Differentiator 85 produces an initially large, transient voltage for an abrupt change in input voltage.

The differentiator's output is fed to the other input of summing amplifier 86. The addition of the differentiated voltage into this circuitry which controls the response of the monitor (as hereinafter explained) improves the dynamic responses of the monitor by a factor of about four.

Summing amplifier 86 combines the differentiator's and the difference amplifier's outputs. The sum of these voltages is then fed to integrator 87 which produces a slowly varying D.C. voltage corresponding to the integral of the difference between the high-filtered and low-filtered rms voltages and the differentiated value of said difference.

Figure 4:
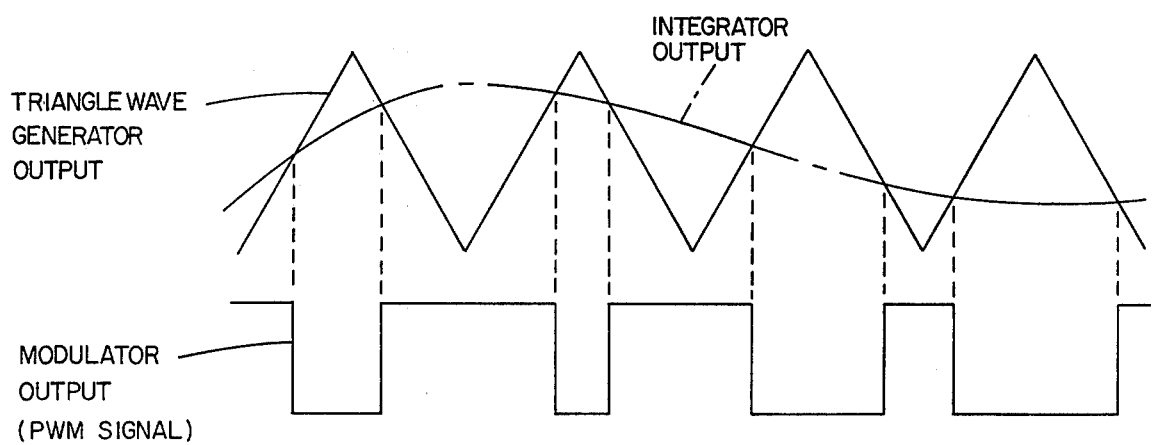
FIG. 4 is a timing diagram of the input and output of a modulator.

The integrated output is fed through sample and hold circuit 88 (to be discussed later) to comparator 92 of the modulator 90. The other input for comparator 92 is from triangle wave generator 94 which operates at about 20 KHz. The integrator signal of FIG. 4 is greatly time-compressed as it has a much lower frequency content than that of the triangle wave. Therefore, changes in pulse width and duty cycle would occur more gradually than represented. As shown in the timing diagram of FIG. 4, the output of comparator 92 is a pulse width modulated (PWM) signal or pulse train, the pulse width (and hence the duty cycle) of which increases or decreases with a corresponding change in the level of the integrator output. The PWM signal is fed to low and high pass filters 16, 18.

The output from sample and hold circuit 88 is also fed to band pass filter 98 which eliminates the D.C. level and sends an amplified A.C. output to zero detector 100. Placement of band pass filter 98 after sample and hold circuit 88 insures stable operation when monitor is used in the hold mode (as hereinafter explained).

Zero detector 100 feeds an input signal from band pass filter 98 into a pair of matched comparators 101, 102 and sends out the resulting signal to clock 104. As long as no voltage is received from zero detector 100, clock 104 provides high frequency clocking pulses for sample and hold circuit 88. The clocking pulses repeatedly enable the sample and hold circuit 88, thus passing a staircased version of the output of integrator 87 to modulator 90.

The output of zero detector 100 is also fed to switches 78, 79, alternate light circuit 108, and event marker driver circuit 114. When the integrator output continues to have significant A.C. variation, no zero is detected. Red light 109 of light circuit 108 is lit, and switches 78, 79 remain closed. If there is no A.C. variation from integrator 87, zero detector 100 produces an output voltage. Green light 110 turns on, and switches 78, 79 are open. Driver circuit 114 enables the event marker of a Gulton Rustrack #500 Strip Chart Recorder 112. Recorder 112 also has scale select switch 116, which controls the recorder chart scale, and a chart drive switch 118, which selectively enables the chart movement of recorder 112.

The RMS circuits 70, 71 also need their respective outputs to meter switch 120 and meter 122. Meter switch 120 is a two-pole, three-position switch which selectively forwards either high or low filtered rms voltage or their difference to meter circuit 122. Meter circuit 122 amplifies the signal from meter switch 120 and sends it to meter 124 for visual display.

The same rms outputs are also fed to mode switch 126, which when closed, feeds the rms voltage to divider circuit 128. Divider circuit 128 produces an output signal which represents the ratio of the two rms voltages. This ratio output is amplified and sent to analog switch 130. Analog switch 130 sets its ratio output to 1 until an initial signal is received. The ratio output of analog switch 130 is sent to recorder's parameter switch 132. Parameter switch 132 also receives the output from sample and hold circuit 88, and either signal can be selected for print out on the recorder 112.

OPERATION

Referring to FIG. 1, surface electrodes 12 are connected to a patient's muscle. A cutoff frequency is selected for filters 16, 18. This selected frequency is usually about 90 Hz, which is in the mid-range of possible median myoelectric frequencies.

When the monitor is activated, the actual myoelectric signal is sensed by electrodes 12 and sent through preamplifier 14 to low and high pass filters 16, 18. If the actual median frequency of the myoelectric signal is above or below the selected cutoff frequency, the low and high filters' rms voltages from RMS circuits 70, 71 will not be the same. When the rms difference is zero the cutoff frequency of the filters approximately equals the true median frequency.

Switches 78, 79 are initially closed, and the different rms voltages are fed into amplifier 80. The amplifier output represents the difference between the rms voltages. If the low pass filter's output is greater than the high pass filter's output, the output of difference amplifier 80 has a negative value. If the opposite were the case, the amplifier output would be positive. This signal passes through differentiator 85 and summing amplifier 86. Integrator 87 then produces the slowly varying D.C. signal which is fed to modulator 90, because sample and hold circuit 88 is initially continuously enabled.

The modulator combines the integrator output with the triangle wave to produce a 20 KHz pulse train which is fed to the switches of filters 16, 18. The filter switches close when they receive a pulse and open for a period of zero voltage. As previously explained, the duty cycle and hence the filters' cutoff frequency directly depend on the length of "on" time for the switches, and as shown in FIG. 4, the level of the integrator output determines this pulse width or "on" time.

Based on the pulse width of the modulator output signal, the filters' cutoff frequency increases or decreases toward the actual median frequency. The rms voltages are compared again and the difference is less. Integrator 87 integrates the new difference to the old, and the cutoff frequency is increased or decreased again towards the real median. This is a continuous process which forces the cutoff frequency of the filters toward close approximation of the true median frequency. In the event the modulator output raises or lowers the filters' cutoff frequency past the actual median, the output of difference amplifier 80 will change sign. The new output will reduce the integrator output thereby correcting the overshoot.

The monitor can operate in a track mode in which the sample and hold circuit 88 is continually enabled, and switches 78, 79 remained closed throughout the test. The track plot records the cutoff frequency of filters 16, 18. The filters' cutoff frequency is continually displayed as it decreases as the median frequency decreases. The decrease in frequency can be real-time recorded in this manner and directly observed as it occurs.

The resulting track mode plot can be directly read for median frequency at any given point. The track plot is also not susceptable to amplitude changes which invariably occur due to a number of factors including patient movement. Finally, track plots for successive tests can be easily compared. There is a fall off at the beginning of each muscle contraction. This is clearly shown by the track plots even if the readouts for different tests were not started at the same time.

The monitor can also function in a hold mode. There, zero detector 100 disables clock 104 when it senses the absence of substantial A.C. variation from the integrator 87. Sample and hold circuit 88 then blocks any signal from integrator 87 and holds the last previous value. At the same time, zero detector 100 switches 78, 79 cutting off any further rms voltages from RMS circuits 70, 71. The cutoff frequency of the filters of the now-balanced monitor is fixed at the initial median frequency. The median frequency of the myoelectric signal decreases as the muscle is fatigued, however, and low pass filter therefore passes increasingly more of the entire signal. As the test progresses, the high filtered voltage decreases with respect to the low filtered voltage. The difference can be seen visually at meter 124 or on the chart of recorder 112. In one embodiment the two voltages are respectively plotted along X and Y axes of a graph, with the resulting polar vector representing the magnitude of the overall myoelectric signal. Alternatively, the ratio of the voltages can be plotted as a function of time.

What is claimed is:

1. A neurological monitor for measuring the spectral variation in a myoelectric signal, comprising
    an electrode suitable for contacting a living being and detecting said myoelectric signal,
    circuitry for processing said myoelectric signal to provide a display signal representative of said spectral variation, said circuitry comprising
        means for amplifying said myoelectric signal to provide an amplified signal,
        filter means for providing a filtered signal corresponding to a portion of said amplified signal having frequency components on one side of a variable cutoff frequency,
        means for comparing said filtered signal to a reference signal and providing a control signal that is dependent on the difference in magnitude between said filtered and reference signals,
        means for automatically varying said cutoff frequency in accordance with the value of said control signal,
        means for providing a display signal representative of said spectral variation in said myoelectric signal, and
    a display driven by said display signal, for observing said spectral variation in said myoelectric signal.

2. The monitor of claim 1 wherein said display comprises a recorder which produces a graph of said cutoff frequencies as a function of time.

3. The monitor of claim 1 wherein said means for comparing comprises a difference amplifier which compares said filtered and reference signals and produces said control signal.

4. The monitor of claim 1 wherein said means for automatically varying comprises means for varying said cutoff frequency in a direction tending to reduce said difference in magnitude.

5. The monitor of claim 1 wherein said means for providing a display signal includes means for deriving said display signal from said control signal.

6. The monitor of claim 1 wherein said circuitry further comprises
    means operative during an initial phase for automatically varying said cutoff frequency in accordance with the value of said control signal until said cutoff frequency becomes equal to a median frequency of said myoelectric signal, and means operative after said initial phase for holding said cutoff frequency constant, and
    wherein said means for providing a display signal includes means for deriving said display signal from said filtered signal after said initial phase.

7. The monitor of claim 6 wherein said means operative during an intitial phase for automatically varying comprises a sample and hold circuit which passes a signal which varies said cutoff frequencies only so long as said circuit receives a clocking signal from a clock.

8. The monitor of claim 7 wherein said means for varying further comprises circuitry for inhibiting said clocking signal when said cutoff frequencies equal said median frequency.

9. The monitor of claim 6 wherein said display comprises means for providing a polar plot on which the respective magnitudes of said filtered and reference signals are plotted along orthogonal axes.

10. The monitor of claim 6 wherein said display comprises means for plotting the magnitude ratio of said filtered signal to said time.

11. The monitor of claim 6 wherein said display is operative only after said initial phase, to display said signal derived from said filtered signal.

12. The monitor of claim 6 wherein said means for deriving said display signal includes means for deriving said signal from the difference between or ratio of said filtered and reference signals.

13. The monitor of claim 5, 6, or 12 wherein said circuitry further comprises a second filtering means for providing a second filtered signal corresponding to a portion of said amplified signal having frequency components on the side of said cutoff frequency opposite that of said first mentioned filtered signal and said reference signal corresponds to said second filtered signal.

14. The monitor of claim 13 wherein said first-mentioned and second filter means comprise a high pass filter and a low pass filter.

15. The monitor of claim 14 wherein said means for automatically varying comprises a modulator wich receives said control signal and sends out a modulated signal to said filters, said modulated signal varying said cutoff frequencies.

16. The monitor of claim 15 further comprising an integrator which continuously intergrates a signal derived from the difference between said filtered and reference signals to generate said control signal.

17. The monitor of claim 16 further comprising a differentiator upstream of said integrator.

18. The monitor of claim 17 further comprising a summing amplifier upstream of said integrator, said summing amplifier combining the output of said differentiator with the undifferentiated signal.

* * * * *